United States Patent
Offen et al.

(10) Patent No.: US 6,722,213 B2
(45) Date of Patent: Apr. 20, 2004

(54) TEMPERATURE-ADJUSTED SAMPLER FOR FLUIDS

(75) Inventors: Reimer Offen, Bargteheide (DE); Jürgen Kiessling, Schlitz-Bernshausen (DE)

(73) Assignee: Minitubes GmbH, Munich (DE)

( * ) Notice: Subject to any disclaimer, the term of this patent is extended or adjusted under 35 U.S.C. 154(b) by 292 days.

(21) Appl. No.: 09/777,610

(22) Filed: Feb. 6, 2001

(65) Prior Publication Data

US 2001/0017060 A1 Aug. 30, 2001

(30) Foreign Application Priority Data

Feb. 6, 2000  (DE) .......................................... 100 04 941

(51) Int. Cl.$^7$ ................................................. G01N 1/00
(52) U.S. Cl. .................................. 73/863.11; 73/304 C
(58) Field of Search ........................... 73/304 C, 863.11, 73/864.23, 864.24, 864.74; 422/100; 366/140

(56) References Cited

U.S. PATENT DOCUMENTS

| | | | | |
|---|---|---|---|---|
| 5,049,826 A | * | 9/1991 | Sasao | 73/864.24 |
| 5,143,849 A | * | 9/1992 | Barry et al. | 436/50 |
| 5,178,019 A | * | 1/1993 | Keiter | 73/864.24 |
| 6,021,253 A | * | 2/2000 | Bell | 73/863.11 |
| 6,148,656 A | * | 11/2000 | Breton | 73/23.31 |
| 6,148,666 A | * | 11/2000 | Roesicke | 73/304 C |

FOREIGN PATENT DOCUMENTS

| | | |
|---|---|---|
| EP | 0 569 851 | 5/1993 |
| WO | WO 97/44133 | 11/1997 |
| WO | WO 98/57180 | 12/1998 |

* cited by examiner

*Primary Examiner*—Robert Raevis
(74) *Attorney, Agent, or Firm*—Vidas, Arrett & Steinkraus, P.A.

(57) ABSTRACT

A temperature-adjusted sampler for liquids, gases or other fluids including a hollow needle in steel or another metal on which a heating is deposited so as to be electrically insulated, characterized in that the hollow needle is coated with an electrically insulating layer which has deposited thereon in complete intimate contact a thin, electrically conducting heating layer.

21 Claims, 6 Drawing Sheets

TEMPERATURE-ADJUSTED SAMPLER FOR FLUIDS

CROSS-REFERENCE TO RELATED APPLICATIONS

Not Applicable

STATEMENT REGARDING FEDERALLY SPONSORED RESEARCH

Not Applicable

BACKGROUND OF THE INVENTION

The invention relates to a temperature-adjusted sampler for fluids, gases or other fluids.

Temperature-adjusted samplers are particularly used in automatic and semiautomatic analyzers for medical science, bio-engineering, environment analytical chemistry, and substance analyses in which liquid, gaseous or other fluid samples or reagents are received, transported, and discharged.

The samples may be adjusted in temperature by means of the temperature-adjusted sampler here. For example, this may be necessary for endogenous liquids, substances or materials which require to be kept to body temperature.

Problems will frequently occur in temperature adjustment, liquid detection, blending, etc. of the samples.

Some known systems and their drawbacks will now be presented:

A hollow needle with a cavity through which temperature-adjusted water or another liquid for adjusting the needle temperature is pumped. The drawback of this system is the growth of bacteria in the temperature-adjusting liquid, which frequently needs to be exchanged for this reason even if it contains additives to prevent the growth of bacteria. Since the exchange of the temperature-adjusting liquid cannot be carried out by the user the servicing expenses are high. Furthermore, the expenditure in devices is high in this system. Adjusting the temperature up to the tip of the hollow needle is impossible because the cavity does not extend up to the tip.

Further, there are hollow needles which are heated by means of a deposited copper jacket using foil heating or a heating coil. The foil heating consists of a foil having a heating layer laminated thereon. The electric conductivity if the foil is relatively bad. The foil heating can only be adhered to hollow needles having a relatively large diameter. The adhesive bond of the foil heating can easily be detached. A further drawback is that heat transfer is too sluggish if cooling (i.e. by ambient temperature) and heating is effected alternately. Furthermore, the outer diameter of the hollow needle is too large with the coatings deposited. Faults in heating and in level detection may arise due to penetrating moisture because of a capillary effect. Precise temperature adjustment up to the tip is impossible and temperature guidance is poor. Another drawback are the great sluggishness, low constancy, and expensive design of this system.

In addition, there are hollow needles using a directly deposited heating coil. Here, the drawbacks only are the linearly shaped heat transfer and too slow and too sluggish a temperture guidance, which mostly necessitates separate pre-heating components. The temperature transient response of this system is unfavourable as well and requires expenditure in temperature regulation.

Due to their construction, all of the aforementioned systems have a large outer diameter so that a relatively long, non-temperature adjusted needle tip is required to dip them into small sample vessels. As a result, very small sample volumes can be treated only conditionally or cannot be treated. Because of their construction, faults in heating and in level detection will frequently occur because of the penetration of moisture or capillary effects. The reasons are the many mechanically assembled components, glued joints, shrunk-on flexible tubes and the like. The two last-mentioned systems using a heating wire or heating foils only have a linearly shaped heat transfer zone and, consequently, are sluggish and inaccurate.

All above mentioned embodiments have the disadvantage that they largely increase the outer diameter of the sampler and heat transfer is relatively slow. The non-heated needle tip which is very long does not allow of precise temperature adjustment, particulary for small sample volumes.

More problems of previous systems are:

Separate stirring devices are used to blend substances. If these have to be displaced as well they will impede any further acceleration of the displacing motions or extend the time for analyses and are expensive.

Piercing through the lids of closed vessels is effected only via separate pre-piercing devices which require increased expenditure in construction and higher expenses for the devices.

Substance entrainments and level detection problems occur because of the multiplicity of components and glued joints, shrunk-on flexible tubes, sensor wires and the like of the previous samplers. The sharp edges, corners, and capillary structures of the former systems may cause substance entrainments which can only be prevented by more expensive washings with cleansing liquid. Longer washing times imply longer cycle times of the analytical instrument end increase the demand of cleansing liquid and the expenditure in disposal. Moisture penetrations into the capillaries may prevent the function of level detection.

Any device to detect needle pluggings has been integrated in very few analytical instruments hitherto and requires great expenditure. Particularly in measuring blood coagulation, there is an increased risk of plugging, which may lead to erroneous measurements and increased times of failure.

Therefore, it is an object of the invention to provide an adjusted-temperature sampler which can be designed at less expenditure and in a smaller cross-section and has more favourable characteristics in use.

BRIEF SUMMARY OF THE INVENTION

In the inventive sampler, the coatings deposited only are very thin so that only an insignificant increase in cross-section will arise. Moreover, the heating layer will rest on the insulating layer respectively the hollow needle with its all-over surface unlike a heating coil or a heating foil. As a result, the heating power is transferred very quickly to the internally lying liquid. The insulating layer may completely or almost completely or partly cover the hollow needle and the heating layer may completely or almost completely or partly cover the insulating layer. The insulating layer may be made up, for example, from glass ceramic material, Teflon, diamond, boron nitride or the like. The heating layer may be made up, for example, from known resistive materials (especially for resistors). The heating layer may be made up, for example, from metals, alloys or semiconductors. Preferably, the heating layer shows a high specific resistance and a high temperature coefficient.

Certain features of the inventive sampler are of a particular advantage when temperature adjustment may be somewhat slower. Glass or plastic may be more favourable for the proportioning of certain fluids or may reduce the production cost of the sampler. Further, an insulating layer can be dispensed with in the case of glass or plastic.

A feature of the inventive sampler enables the user to easily exchange the sampler. The device may be an analytical instrument which, in particular, may have a displacement device to be connected to the hollow needle and an electrical supply device for the heating layer. The hollow needle may be detachably connected within an analytical instrument by a bolted joint to a flexible pipetting tube and the flexible pipetting tube may be connected to the displacement device of the analytical instrument.

A feature of the inventive sampler makes it possible to save a temperature sensor. Furthermore, it allows to average a temperature over the length of the electrically conducting heating layer which is disposed very close to the sample so that a good regulation will result.

A calibration feature of the inventive sampler helps ensure that the requirements for accuracy of the coatings of the hollow needle are low.

Almost all samplers are equipped with a liquid or level detection which either:

measures the resistance between two contacts or measures the capacitance between the hollow needle and the surface of the associated instrument.

The two techniques have some advantages each. In the first one, for example, it cannot be differentiated whether the sampler merely is wetted by a small liquid volume or is dipped. In the second technique, the evaluation of the measuring signal involves relatively great expenditure. Moreover, the surface of the instrument requires to have a good connection to the electrical mass.

A feature of the inventive sampler overcomes the aforementioned difficulties and solves the initially described problems of substance entrainment and level detection. The capacitance is measured according to a principle which simplifies evaluation very much and is adaptable to the various requirements of the software. An electric pulse is provided to the hollow needle here. The rise time of the edge of this pulse is determined by the capacitance between the hollow needle and the electrical mass and by the internal resistance of the pulse. The magnitude of capacity may be determined by measuring the voltage on the hollow needle following a short lag time after the pulse is applied. At this time, the lag time requires to be kept constant.

A feature of the inventive sampler makes it possible to detect the liquid by measuring the resistance. In addition, there is a possibility to combine the capacitive and the resistive liquid detection.

The sampler may operate as a blending device, e.g. in an automatic instrument, in which liquid samples are transferred to a blending duct where reagents are added, and are thoroughly blended. This has been made by a separate mixer hitherto. If the hollow needle is caused to vibrate by an electromagnet or ultrasound the sampler will assume this task.

A feature of the inventive sampler makes it possible to pierce the sampler through a lid and to deeply dip it into a liquid. To this effect, the further coating requires to be very hard. Diamond and boron nitride serve the purpose here, for example.

A feature of the inventive sampler prevents a vacuum from building up after the sampler is pierced through the sample closures, which partly have a very high wall thickness and are made from rubber or similar materials, while the sample is drawn in from the vessel. This can reduce the accuracy of dosage of the sample. The slots will generally not inadmissibly weaken the sampler because this one is of a greater wall thickness anyhow to achieve a high puncturing force and buckle proofness for piercing through the lid. In particular, the slots may be configured as milled sinks. Generally, a single slot is sufficient. Several slots preferably are uniformly spaced around the circumference of the sampler. Preferably, the slots are inclined at an angle to the center of the needle. Hereby, the material of the sample closure (i.e. rubber) is hindered to penetrate and obdurate the slots.

A feature of the inventive sampler makes it possible to detect a plugging of the hollow needle while receiving liquids because a pressure drop may be measured and detected in such case. The pressure sensors may be wire strain gauges, foil-type pressure gauges, and others.

A feature of the inventive sampler integrates the ultrasonic transmitter of claim 16 into the coatings. This manner of ultrasound generation was described in "Nature", vol. 400, page 853. Ultrasound may also be employed to clean the sampler.

A feature of the inventive sampler achieves a safe insulation because so-called pinholes (small-diameter holes) in a part-layer are covered by an adjoining part-layer. This utilizes the fact that it is extremely unlikely for pinholes to occur at the same point in the part-layers that cover each other.

BRIEF DESCRIPTION OF THE SEVERAL VIEWS OF THE DRAWINGS

The invention will now be explained in more detail with reference to the accompanying drawings of embodiments. In the drawings.

DETAILED DESCRIPTION OF THE INVENTION

While this invention may be embodied in many different forms, there are described in detail herein a specific preferred embodiment of the invention. This description is an exemplification of the principles of the invention and is not intended to limit the invention to the particular embodiment illustrated.

Identical components are designated by the same reference numbers in the following description of various embodiments.

Figure 1:
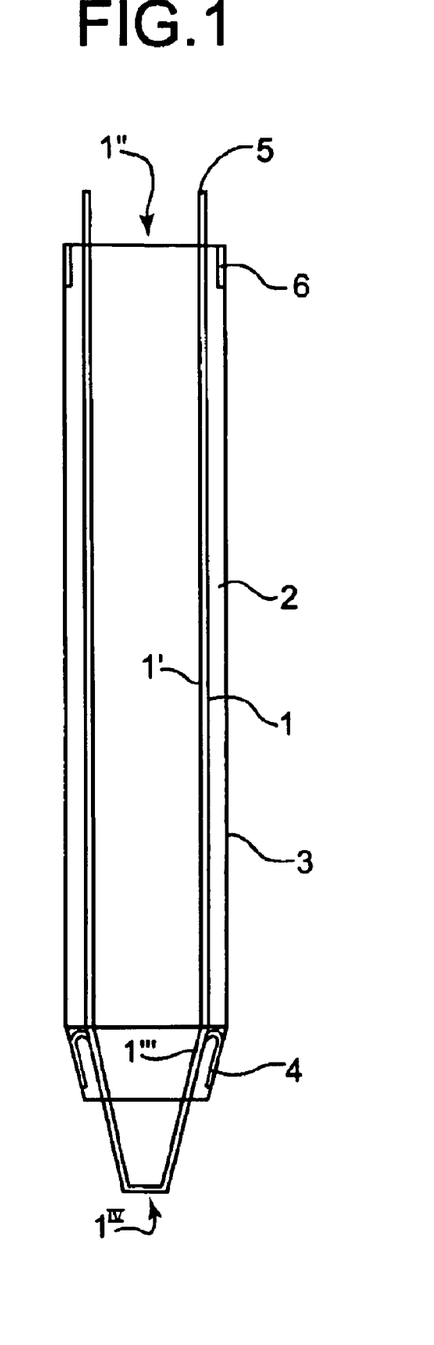
FIG. 1 shows a longitudinal section of a temperature-adjusted sampler including an electrically conducting heating layer which makes contact with the hollow needle in steel in the vicinity of the tip.

The sampler of FIG. 1 has a hollow needle 1 in steel or another electrically conductive material, which has a cylindrical portion 1' with an end-sided aperture 1" and a conical tip portion 1''' with a tip aperture 1$^{IV}$ at the other end.

To receive a sample, the aperture 1" of the hollow needle 1 is connected to a displacement system (e.g. a cylinder and a piston movable therein). The displacement of air by means of the displacement system then makes it possible to draw a fluid sample into the hollow needle 1 through the tip aperture 1$^{IV}$ and to discharge it again therefrom through the tip aperture 1$^{IV}$. The sample which is in the hollow needle 1 is adjustable in temperature, for which purpose the sampler has the components which now follow:

The insulating layer 2 is deposited over nearly the whole length of the cylindrical portion 1' of the hollow needle 1. The outside of the insulating layer 2, in turn, has deposited thereon an electrically conducting heating layer 3 covering the complete surface of the insulating layer 2 or an essential portion thereof. The electrically conducting heating layer 3 projects beyond the lower end of the insulating layer 2 in the area of the conical tip portion 1'" and is in an electric connection to the hollow needle 1 there in the connecting area 4.

The upper end of the hollow needle 1, which projects beyond the insulating layer 2 and the heating layer 3, constitutes a circumferential electric contact 5. Furthermore, the upper edge of the heating layer 3 is connected to a circumferential contact 6.

In its upper area, the sampler can be removably attached to an analytical instrument, especially by insertion or snapping in. To this end, a connection of the aperture 1" is made to a displacement device of the analytical instrument and an electric connection of the contacts 5, 6 is made to an electric supply device or the electronic unit of the analytical instrument. This makes it possible to both draw in a sample into the hollow needle and discharge it therefrom and to adjust the temperature of the hollow needle 1 and, hence, a sample received by means of an electric current through the heating layer 3. Moreover, the analytical instrument makes it possible to transport the sample in the sampler.

Figure 2:
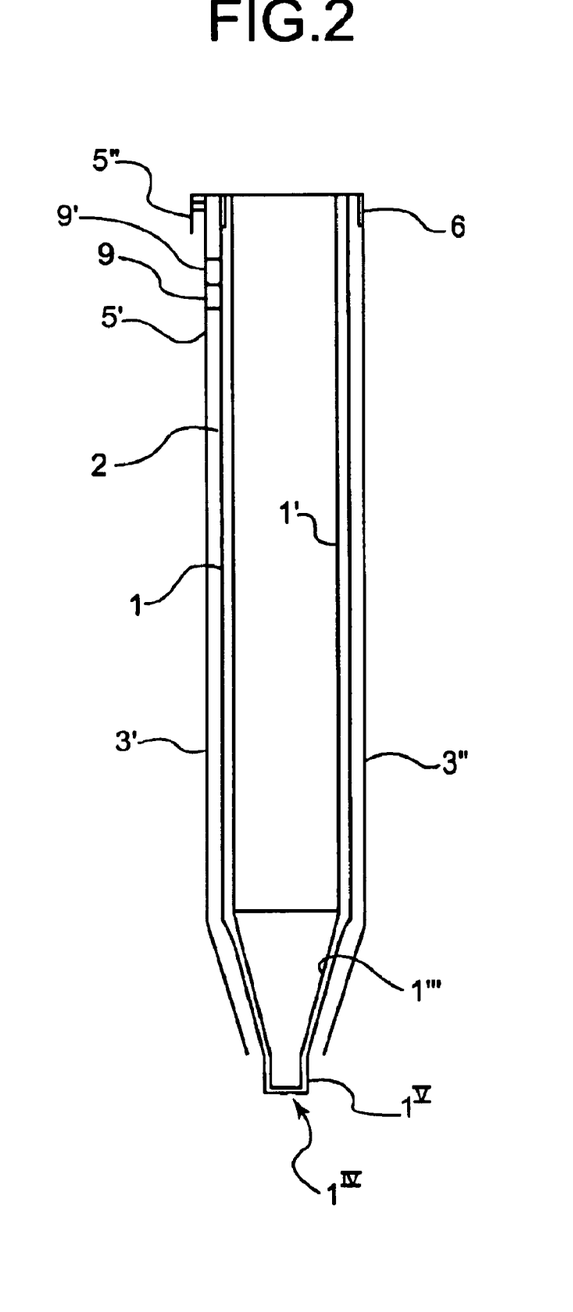
FIG. 2 shows a longitudinal section of a temperature-adjusted sampler including an electrically conducting heating layer in the shape of two half-cups.
Figure 3:
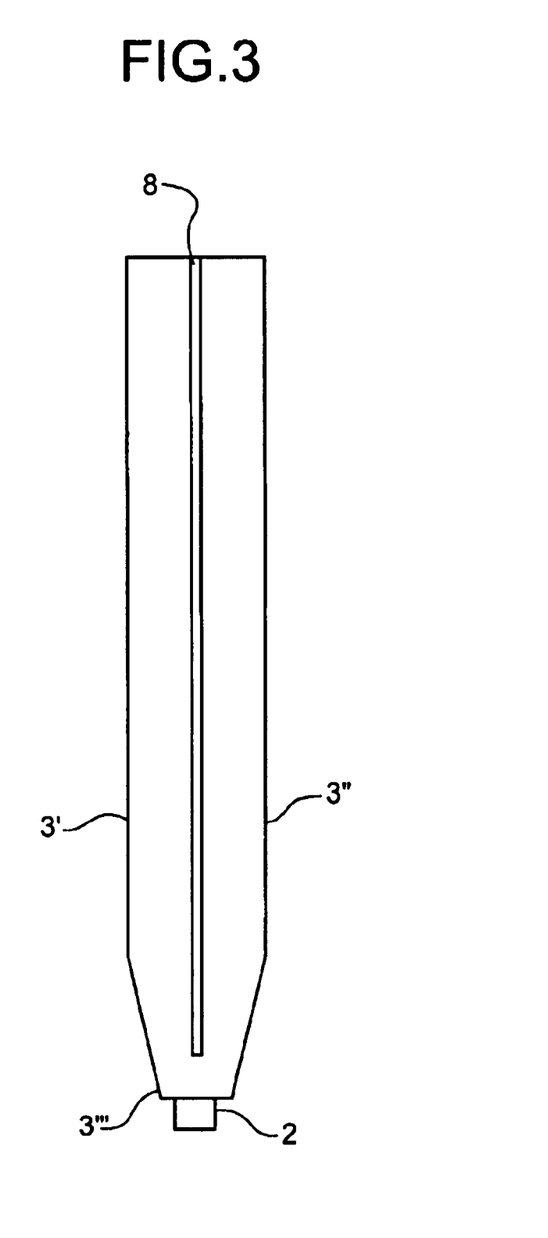
FIG. 3 shows a side view of the temperature-adjusted sampler of FIG. 2.

The sampler of FIGS. 2 and 3 distinguishes itself from the one described above in that the front end of the conical tip portion 1''' is adjoined by a small cylindrical tip portion 1$^V$ of the hollow needle, which has the tip aperture 1$^{IV}$.

Furthermore, the insulating layer 2 is drawn downwards onto the cylindrical tip portion 1$^V$ over the conical tip portion 1'''.

Figure 4:
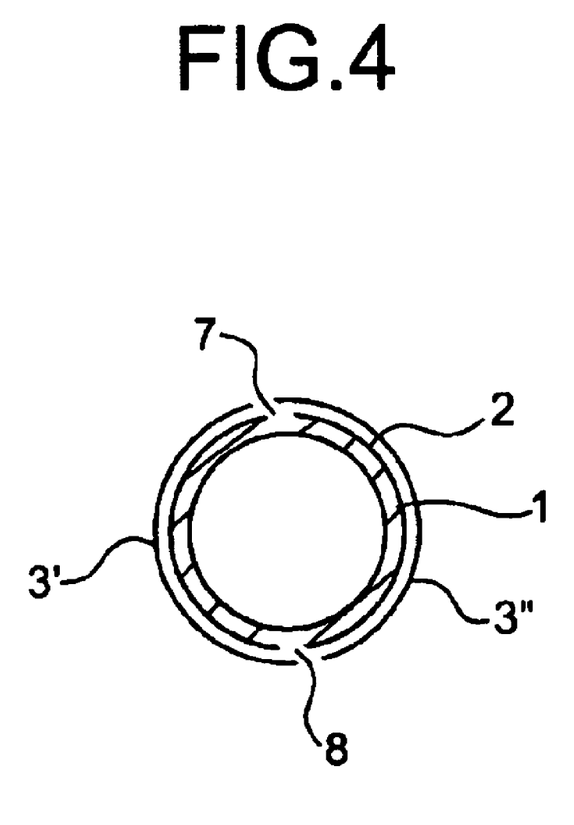
FIG. 4 shows a cross-section of the temperature-adjusted sampler of FIGS. 2 and 3.

Further, the heating layer 3 is configured in the shape of two half-cups 3', 3" between which a slot 7, 8 is formed on either side of the sampler. The slots 7, 8 are formed by milled sinks which extend into the hollow needle 1. The milled sinks 7, 8 are inclined at an angle to the radius of the hollow needle 1 and are disposed opposite each other. They extend from the upper edge of the sampler up to the level of the conical tip portion 1'''. The half-cups 3', 3" are in an electrical interconnection 3''' underneath.

The half-cup 3' is interrupted by a half ring-shaped layer made of porous silicon 9 near the upper end of the sampler. The half-cup 3' comprises an upper portion beginning from the upper end of hollow needle 1 and covering the layer made of porous silicon 9. This upper portion of the half-cup 3' is separated from a lower portion of the half-cup 3' which is provided below the layer made of porous silicon 9. The electrically conductive half-cup 3' has an electric contact 5', 5" each on either side of the layer 9.

The other electrically conductive heating layer 3" also has a contact 6 at the upper end.

Connecting the contacts 5', 6 to an electric power supply makes it possible to heat a sample in the hollow needle 1. If the contacts 5" and 6 are connected to an electric power supply the layered structure in the upper area of the sampler generates ultrasonic waves which may be used for blending purposes. This is effected by heating of layer 9. Additionally by connecting the contacts 5 and 6 to an electric power supply may simultaneously cause the sampler to be heated.

The slots 7, 8 allow to balance the pressure while the sampler is being pierced through the lid of a sample vessel.

Figure 5:
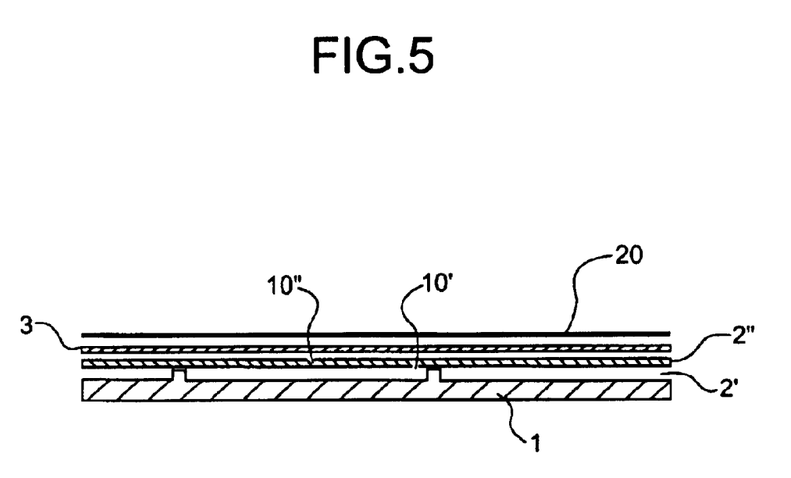
FIG. 5 shows an enlarged partial section of the layered structure in a temperature-adjusted sampler including an insulation layer made up from insulating part-layers lying on top of each other.

According to FIG. 5, a hollow needle 1 in steel has two insulating part-layers 2', 2" lying on top of each other. There is an electrically conductive heating layer 3 on the topmost insulating part-layer 2".

Figure 6:
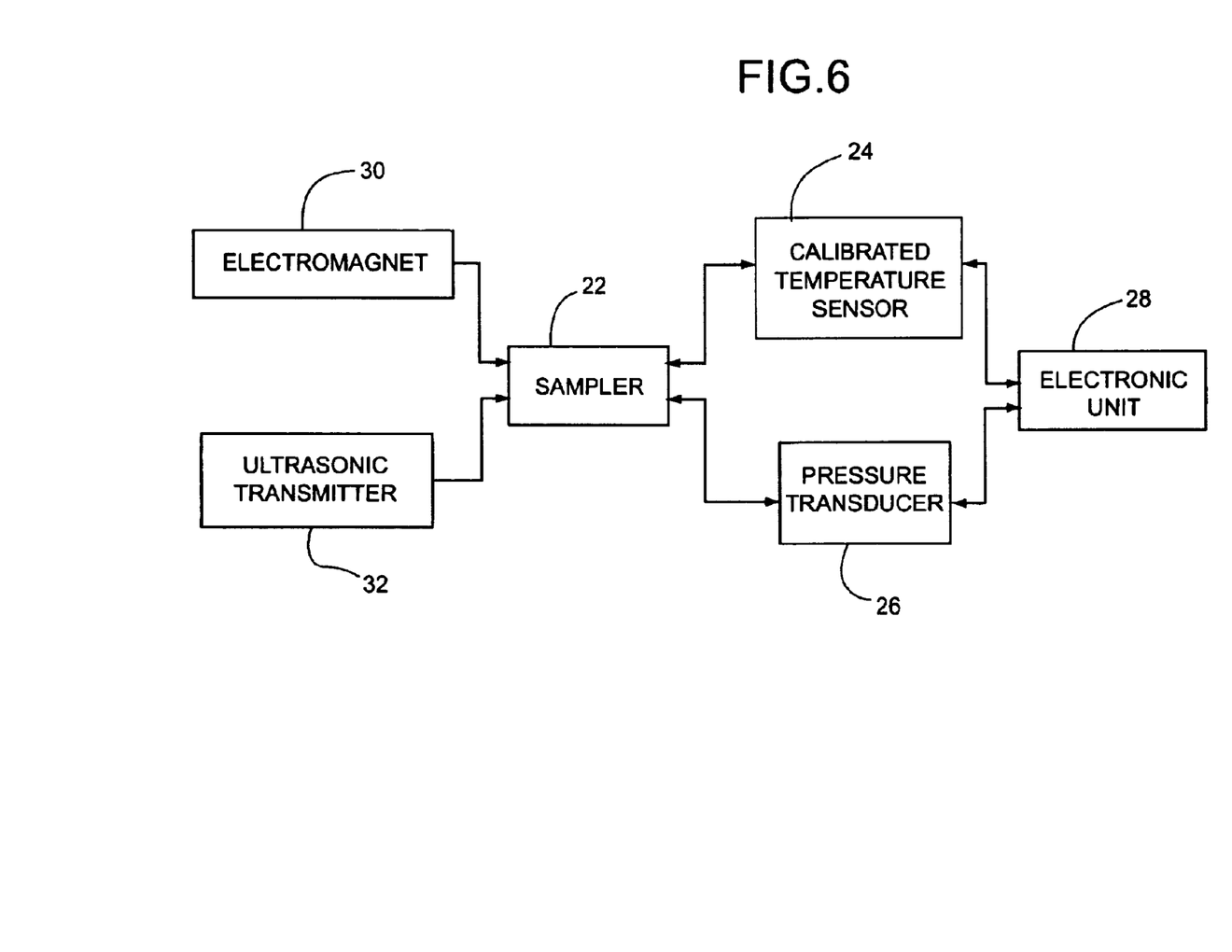
FIG. 6 shows a block diagram of the inventive sampler.

Any pinholes 10', 10" that exist in a random distribution in the insulating part-layers 2', 2" are extremely likely not to cover each other so that insulation is ensured by the insulating layer formed as a whole by the part-layers 2', 2". FIG. 6 shows a block diagram of the inventive sampler in which the sampler is shown at 22. An electronic unit 28 is connected to a calibrated temperature sensor 24 and a pressure transducer 26, both of which are in turn connected to sampler 22 The sampler may be vibrated using either an electromagnet 30 or an ultrasonic transmitter 32.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

List of Reference Numbers
1 Hollow needle
1' Cylindrical portion
1" Aperture
1'" Conical tip portion
1$^{IV}$ Tip aperture
1$^V$ Cylindrical tip portion
2 Insulating layer
2', 2" Insulating part-layers
3 Heating layer
3', 3" Half-cups
3', " Electric interconnection of half-cups
4 Connecting region
5, 6 Contacts
5', 5" Contacts
7, 8 Slots
9 Porous silicon
10', 10" Pinholes

What is claimed is:

1. A temperature-adjusted sampler fluids including a hollow needle (1) on which a heating is deposited so as to be electrically insulated, characterized in that the hollow needle (1) is coated with an electrically insulating layer (2) which has deposited thereon in complete intimate contact a thin, electrically conducting heating layer (3).

2. The sampler according to claim 1, characterized in that the thin, electrically conducting heating layer (3) is extended far towards the tip of the hollow needle (1).

3. The sampler according to claim 1, characterized in that the thin, electrically conducting heating layer (3) in metal vapour-deposited or sputtered or plasma coated on the electrically insulating layer (2).

4. The sampler according to claim 1, including a tip, characterized in that the insulating layer (2) is not extended up to the tip of the hollow needle (1) and the electrically conducting heating layer (3) projects beyond this insulating layer (2) onto the tip and makes electrical contact (4) with the hollow needle (1) there.

5. The sampler according to claim 1, characterized in that the electrically conducting heating layer (3) is deposited in the shape of two half-cups (3', 3") which are electrically interconnected at one end.

6. The sampler according to claim 1, characterized in that the hollow needle (1) is made of glass or plastic.

7. The sampler according to claim 6, characterized in that the hollow needle (1) is made of a flexible plastic tube or of a glass tube.

8. The sampler according to claim 1, characterized in that the coated hollow needle (1) has a detachable connection to a device and/or the electrically conducting layer (3) is electrically connected to the device via clip contacts (5, 6).

9. The sampler according to claim 1, characterized in that there is an electronic unit to cyclically measure the resistance of the electrically conducting heating layer (3), to determine a current pulse length owing to the resistance measured, and provide a corresponding current pulse to the heating layer (3).

10. The sampler according to claim 9, characterized in that the electronic unit is calibrated by means of a temperature-adjusted water bath.

11. The sampler according to claim 9, characterized in that a calibrated temperature sensor, which bears on the sampler from outside, exists to calibrate the electronic unit.

12. The sampler according to claim 1, characterized in that there is an electronic unit to detect the immersion of the sampler in a liquid by measuring the varying capacitance in a way that a discharge graph is measured and evaluated at two times.

13. The sampler according to claim 1, characterized in that at least one half-cup (3', 3") of the heating layer (3) extends up to 2 mm from the tip of the hollow needle (1) and the insulating layer (2) and, the heating layer and insulating layer are designed to be anti-adhesive (hydrophobic) or adhesive (hydrophilic).

14. The sampler according to claim 1, characterized in that there is an electromagnet to cause the sampler to vibrate for the blending operation.

15. The sampler according to claim 1, characterized in that there is an ultrasonic transmitter to cause the sampler to vibrate for the blending operation.

16. The sampler according to claim 1, characterized in that the heating layer (3) has deposited thereon a further substance-repellent, adhesive (hydrophilic) or anti-adhesive (hydrophobic) coating and/or a very hard coating which serves the electrical insulation to the outside and mechanical protection.

17. The sampler according to claim 1, characterized in that slots (7, 8) are created in the longitudinal direction of the hollow needle (1) by the construction and arrangement of the heating layer 3.

18. The sampler according to claim 1, characterized in that there is a pressure transducer to monitor the pressure in the sampler while fluids are being received and discharged.

19. The sampler according to claim 1, characterized in that a portion of the sampler, between the insulating layer (2) and the heating layer (3), has deposited thereon porous silicon (9) to generate ultrasonic waves by means of heating.

20. The sampler according to claim 1, characterized in that the insulating layer (2) is deposited in at least two insulating part-layers (2', 2") lying on top of each other.

21. The sampler of claim wherein the needle (1) is made of metal.

* * * * *